US010485504B2

United States Patent
Arima

(10) Patent No.: US 10,485,504 B2
(45) Date of Patent: Nov. 26, 2019

(54) RADIOGRAPHING SYSTEM FOR OBTAINING A DOSE INDEX FROM A GENERATED COMPOSITION IMAGE

(71) Applicant: CANON KABUSHIKI KAISHA, Tokyo (JP)

(72) Inventor: Keisuke Arima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 91 days.

(21) Appl. No.: 15/636,512

(22) Filed: Jun. 28, 2017

(65) Prior Publication Data

US 2018/0008224 A1 Jan. 11, 2018

(30) Foreign Application Priority Data

Jul. 7, 2016 (JP) .................................. 2016-135413

(51) Int. Cl.
*A61B 6/00* (2006.01)
*G06K 9/46* (2006.01)
*G06K 9/62* (2006.01)
*G06T 7/00* (2017.01)
*G06T 11/60* (2006.01)

(52) U.S. Cl.
CPC ............ *A61B 6/5235* (2013.01); *A61B 6/463* (2013.01); *A61B 6/5211* (2013.01); *A61B 6/5241* (2013.01); *A61B 6/542* (2013.01); *G06K 9/4604* (2013.01); *G06K 9/6202* (2013.01); *G06T 7/0012* (2013.01); *G06T 11/60* (2013.01); *A61B 6/461* (2013.01); *G06T 2207/10016* (2013.01); *G06T 2207/10124* (2013.01)

(58) Field of Classification Search
None
See application file for complete search history.

(56) References Cited

U.S. PATENT DOCUMENTS

| | | | |
|---|---|---|---|
| 2008/0103834 A1* | 5/2008 | Reiner | G06Q 10/0637 705/3 |
| 2009/0161818 A1* | 6/2009 | Sakurai | A61N 5/1048 378/15 |
| 2014/0086390 A1 | 3/2014 | Nakatsugawa | |
| 2014/0093043 A1 | 4/2014 | Nakatsugawa | |
| 2014/0219420 A1 | 8/2014 | Ishikawa | |
| 2017/0021195 A1* | 1/2017 | Schweizer | A61N 5/1039 |

FOREIGN PATENT DOCUMENTS

JP          2016-73508 A        5/2016

\* cited by examiner

*Primary Examiner* — Idowu O Osifade
(74) *Attorney, Agent, or Firm* — Canon U.S.A., Inc., IP Division

(57) ABSTRACT

A radiographing system that can attach a dose index for a composition image and perform dose management in a composition image is provided. The radiographing system includes: a dose index calculation unit configured to respectively calculate dose indices from a plurality of radiographic images, an obtaining unit configured to obtain a representative dose index from among the plurality of dose indices calculated by the dose index calculation unit, and a storage unit configured to store the representative dose index together with the composition image.

17 Claims, 8 Drawing Sheets

| IMAGE ID | EI | X-RAY TUBE VOLTAGE | X-RAY TUBE CURRENT | IRRADIATION TIME |
|---|---|---|---|---|
| 001 | 100 | V1 | I1 | T1 |
| 002 | 110 | V2 | I2 | T2 |
| 003 | 105 | V3 | I3 | T3 |

| IMAGE ID | EI | X-RAY TUBE VOLTAGE | X-RAY TUBE CURRENT | IRRADIATION TIME |
|---|---|---|---|---|
| 002 | 110 | V2 | I2 | T2 |

US 10,485,504 B2

RADIOGRAPHING SYSTEM FOR OBTAINING A DOSE INDEX FROM A GENERATED COMPOSITION IMAGE

BACKGROUND OF THE INVENTION

Field of the Invention

The present invention relates to a radiographing system configured to irradiate a subject with radiation and capture a radiographic image, a management method for a dose index, and a storage medium.

Description of the Related Art

Up to now, a radiographing system provided with a radiation detecting apparatus has been proposed which is configured to irradiate a subject with radiation (for example, X-rays) and capture a radiographic image of a target by detecting an intensity distribution of the radiation that has transmitted through the subject.

When an examination using the radiation (radiation examination) is performed, in general, examination information including an imaging site, an imaging method, and the like is set by doctors in respective medical departments. Then, radiographic imaging is executed by using the radiographing system on the basis of the set examination information.

In addition, dose management in the radiographic image captured by the radiographing system is performed. For example, according to Japanese Patent Laid-Open No. 2016-73508, a dose index measured from the radiographic image is stored, and a warning is issued in a case where a difference occurs in the dose index for the next imaging. However, according to Japanese Patent Laid-Open No. 2016-73508, no descriptions are given on performance of the dose management in a composition image obtained by combining a plurality of radiographic images with one another. That is, since the dose index is not attached to the composition image, it is difficult to perform the dose management in the composition image.

SUMMARY OF THE INVENTION

According to an aspect of the present invention, a radiographing system that generates a composition image by combining a plurality of radiographic images with one another includes a dose index calculation unit configured to analyze each of the plurality of radiographic images and calculate a plurality of dose indices corresponding to the plurality of radiographic images, an obtaining unit configured to obtain a representative dose index from among the plurality of dose indices calculated by the dose index calculation unit, and a storage unit configured to store the representative dose index together with the composition image.

Further features of the present invention will become apparent from the following description of exemplary embodiments with reference to the attached drawings.

DESCRIPTION OF THE EMBODIMENTS

Hereinafter, exemplary embodiments of the present invention will be described with reference to the accompanying drawings. Each of the embodiments of the present invention described below can be implemented solely or as a combination of a plurality of the embodiments or features thereof where necessary or where the combination of elements or features from individual embodiments in a single embodiment is beneficial.

First Exemplary Embodiment

A radiographing system according to a first exemplary embodiment of the present invention will be described with reference to FIG. 1.

Figure 1:
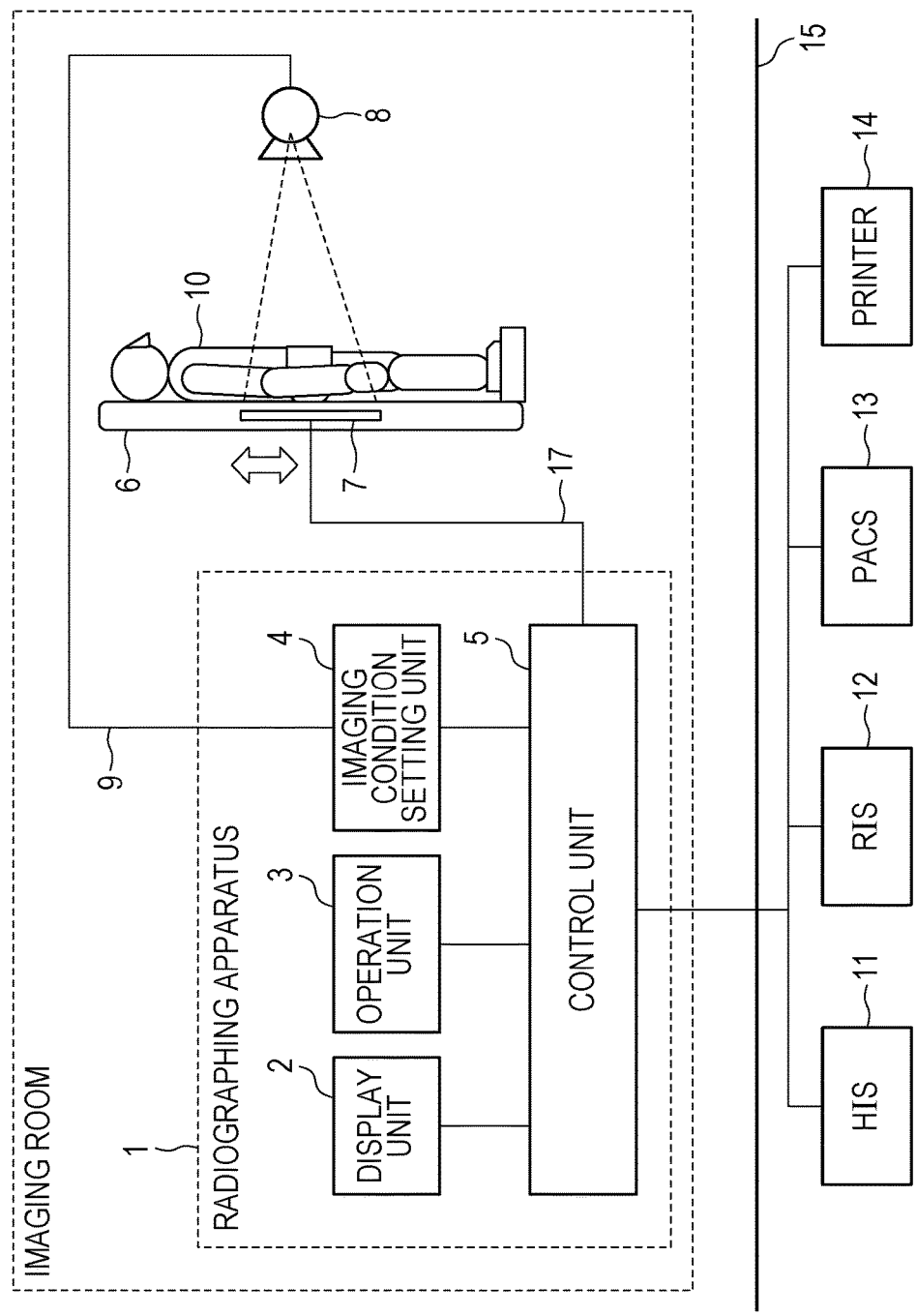
FIG. 1 illustrates an overall configuration of a radiographing system according to an exemplary embodiment of the present invention.

As illustrated in FIG. 1, the radiographing system is provided with a radiographing apparatus 1, a hospital information system (HIS) 11 configured to manage a progress of an examination, and a radiology information system (RIS) 12 configured to transmit an examination order to the radiographing apparatus 1. In addition, a picture archiving and communication systems (PACS) 13 configured to manage a radiographic image and a printer 14 configured to print and output the radiographic image are connected to the radiographing system.

The HIS 11 is a hospital management system and includes a server configured to manage accounting information. In a case where radiographic imaging is performed, an operator inputs an examination instruction from a terminal of the HIS 11. Then, the examination instruction is transmitted from the HIS 11 to a radiation department of a hospital at a request destination. This request information is referred to as an examination order. The examination order includes a department name at a request source, an examination item, individual data of the subject, and the like.

When the examination order is received in the RIS 12, the radiation department adds information related to the radiographic imaging to the examination order and transmits the examination order to the radiographing apparatus 1. The radiographic imaging is executed by using the radiographing apparatus 1 in accordance with the received examination order. The radiographing apparatus 1 adds examination information including the examination order to the captured radiographic image.

The PACS 13 is a server configured to perform image management as a main purpose. An image inspection operation, detailed post-treatment, and diagnosis operation of the radiographic image are executed by a high definition monitor connected to the PACS 13. In this manner, the radiographic image captured by the radiographing apparatus 1 is transmitted to the PACS 13.

In addition, execution information of the examination by the radiographing apparatus 1 is transmitted to the HIS 11. The execution information transmitted to the HIS 11 is also used for accounting processing after the examination in addition to the progress management of the examination.

The radiographing apparatus 1, the HIS 11, the RIS 12, the PACS 13, and the printer 14 are connected with one another via a network 15 constituted by a local area network (LAN), a wide area network (WAN), or the like, for example. It should be noted that the respective apparatuses include one or a plurality of computers. The computer is provided, for example, with a main control unit such as a central processing unit (CPU) and a storage unit such as a read only memory (ROM) or a random access memory (RAM). In addition, the computer may be provided with a communication unit such as a network card, an input and output unit such as a key board, a display, or a touch panel, and the like. The respective component units are connected with one another by a bus or the like and controlled while the main control unit executes a program stored in the storage unit.

As illustrated in FIG. 1, the radiographing apparatus 1 that performs the radiographic imaging is installed in an imaging room. In addition, a radiation generating unit 8 configured to generate radiation, a radiation detecting apparatus 7 configured to detect the radiation that has passed through a subject 10, and an imaging table 6 that supports the radiation detecting apparatus 7 are installed in the imaging room.

The radiographing apparatus 1 is provided with a display unit 2 configured to display the radiographic image, an operation unit 3 with which the operator performs an operation, an imaging condition setting unit 4 configured to set an imaging condition (X-ray tube voltage, X-ray tube current, and irradiation time) with respect to the radiation generating unit 8, and a control unit 5 configured to control the respective components.

The imaging condition setting unit 4 is connected to the radiation generating unit 8 via a cable 9. The imaging condition setting unit 4 sets the imaging condition for the radiation in the radiation generating unit 8 and controls the radiation generating unit 8. The radiation generating unit 8 functions as a radiation source that generates radiation. The radiation generating unit 8 is realized, for example, by a radiation X-ray tube and emits the radiation towards the subject 10 (for example, a particular site of the subject).

The radiation generating unit 8 can emit the radiation in a desired irradiation range. The radiation generating unit 8 is installed via a supporting unit (not illustrated) installed on a floor surface or a ceiling. A diaphragm (not illustrated) that shields the radiation is installed on an irradiation surface of the radiation generating unit 8. When the operator controls the diaphragm that shields the radiation, it is possible to set the irradiation range of the radiation emitted from the radiation generating unit 8.

The radiographing system is provided with the radiation detecting apparatus 7 configured to detect the radiation emitted from the radiation generating unit 8. The radiation detecting apparatus 7 is configured to detect the radiation that has passed through the subject 10 and output image data in accordance with the radiation. It should be noted that the image data can also be rephrased as a radiographic image.

Specifically, the radiation detecting apparatus 7 detects the radiation that has transmitted through the subject 10 as charges equivalent to a transmitted radiation dose. For example, a direct conversion type sensor configured to directly convert the radiation into the charges such as a-Se that coverts the radiation into the charges or an indirect conversion type sensor using a scintillator such as CsI and a photoelectric conversion element such as a-Si is used as the radiation detecting apparatus 7. Furthermore, the radiation detecting apparatus 7 generates the image data by performing an analog-to-digital (A/D) conversion of the detected charges to be output to the control unit 5.

The radiation detecting apparatus 7 is accommodated in the imaging table 6. The imaging table 6 is a rectangular casing, and the inside of the casing is hollow. In addition, the imaging table 6 has a function for holding the radiation detecting apparatus 7 and also performing vertical movements of the radiation detecting apparatus 7. The radiation detecting apparatus 7 can be slid along a longitudinal direction of the imaging table 6. While the radiation detecting apparatus 7 is slid, radiation is emitted plural times from the radiation generating unit 8 for imaging, so that it is possible to perform stitch imaging of the subject 10.

As illustrated in FIG. 1, the imaging table 6 is installed in a manner that the imaging table 6 is upright with respect to the floor surface. The subject 10 is installed along the longitudinal direction of the imaging table 6. The imaging table 6 has a supporting function for supporting the subject 10.

The imaging table 6 is installed in a manner that the longitudinal direction of the imaging table 6 becomes a vertical direction, that is, the imaging table 6 becomes upright with respect to the floor surface. It should be noted that the imaging table 6 may be installed in a manner that the longitudinal direction of the imaging table 6 becomes a horizontal direction, that is, the imaging table 6 becomes parallel with the floor surface.

The operation unit 3 performs the operation in the radiographing apparatus 1. The display unit 2 is realized, for example, by a liquid crystal display or the like and displays the respective pieces of information towards the operator (such as an imaging operator or a doctor). The operation unit 3 is constituted, for example, by a mouse, an operation button, or the like and inputs the respective instructions from the operator to the respective components. It should be noted that the display unit 2 and the operation unit 3 may be realized as a touch panel in which the display unit 2 and the operation unit 3 are integrated with each other.

The control unit 5 of the radiographing apparatus 1 is connected to the radiation detecting apparatus 7 via a cable 17. Power supply, image data, control signals, and the like are exchanged between the control unit 5 and the radiation detecting apparatus 7 by using the cable 17. The radiation detecting apparatus 7 detects the radiation that has transmitted through the subject 10 and obtains the radiographic image (image data) based on the subject. That is, the radiation generating unit 8 and the radiation detecting apparatus 7 operate in cooperation with each other to perform the imaging.

The radiographing apparatus 1 receives one or a plurality of examination orders of the radiographic imaging from the RIS 12. The examination order includes, for example, the subject information and one or a plurality of imaging sites of the subject.

The control unit 5 instructs start of the radiographic imaging corresponding to at least one of the received examination orders. Herein, the start instruction is issued, for example, when the operation unit 3 receives an input of the operator. Alternatively, the imaging start may be instructed when the control unit 5 selects the examination order for the imaging to be performed.

Information (first signal) indicating that the radiographic imaging with regard to the examination order is started is transmitted to the HIS 11 in accordance with the imaging start instruction. As a result, a status with regard to the examination order is changed in the HIS 11 to be set as a status indicating that the examination is started. Thereafter, when all the radiographic imaging operations corresponding to the examination order are ended and the operator performs an input for confirming the completion of the examination order via the operation unit 3, the control unit 5 transmits information (second signal) indicating that the examination with regard to the examination order is ended is transmitted to the HIS 11. As a result, the HIS 11 changes the status of the order to be set as a status indicating that the examination is ended.

The radiographing system according to the exemplary embodiment of the present invention will be described in detail with reference to FIG. 2. The radiographing system is provided with the control unit 5 configured to perform image processing on the radiographic image output from the radiation detecting apparatus 7 and generate the image. The control unit 5 has a function of combining the plurality of radiographic images with one another to generate a composition image (lengthy image, stitched image). The control unit 5 also has a function of calculating dose indices from the plurality of radiographic images and obtaining a representative dose index from among the plurality of dose indices to store the composition image together with the representative dose index.

The control unit 5 is connected to the radiation detecting apparatus 7. Specifically, the control unit 5 is connected to the radiation detecting apparatus 7 by a wired or wireless network or a dedicated-use line. The radiation detecting apparatus 7 images the radiation emitted from the radiation generating unit 8 and outputs the radiographic image to the control unit 5. The control unit 5 has an application function for operating on the computer. The control unit 5 controls the operation of the radiation detecting apparatus 7 and also outputs the radiographic image and a graphical user interface to the display unit 2.

The imaging condition setting unit 4 sets the imaging condition (X-ray tube voltage, X-ray tube current, and irradiation time) of the radiation emitted from the radiation generating unit 8. The control unit 5 controls a timing of the irradiation of the radiation generating unit 8 and a timing of the imaging of the radiation detecting apparatus 7. The control unit 5 emits radiation plural times from the radiation generating unit 8, and the radiation detecting apparatus 7 performs the imaging plural times in accordance with the irradiation from the radiation generating unit 8.

That is, the control unit 5 causes the radiation detecting apparatus 7 to perform the imaging plural times, so that the radiation detecting apparatus 7 can output the plurality of radiographic images.

The control unit 5 has a function of performing image processing such as noise removal with respect to the radiographic image output from the radiation detecting apparatus 7. In addition, the control unit 5 can perform image processing such as trimming and rotation with respect to the radiographic image output from the radiation detecting apparatus 7. The display unit 2 displays the radiographic image output from the control unit 5.

As illustrated in FIG. 1, the subject 10 stands on a stepstool placed on the imaging table 6 and is positioned with respect to the radiation detecting apparatus 7 and the radiation generating unit 8. According to the present exemplary embodiment, an angle is set at which the radiation is incident so as to be perpendicular to a center of the radiation detecting apparatus 7. The radiation emitted from the radiation generating unit 8 towards the radiation detecting apparatus 7 transmits through the subject 10 and reaches the radiation detecting apparatus 7 to be detected. Then, the operator slides the radiation detecting apparatus 7 in the vertical direction. The radiation emitted towards the radiation detecting apparatus 7 slid in the vertical direction transmits through the subject 10 and reaches the radiation detecting apparatus 7 to be detected. The plurality of radiographic images obtained in the radiation detecting apparatus 7 are subjected to composition processing by the control unit 5, and the composition image of the subject 10 is generated. The composition image is a lengthy image obtained by the stitch imaging in which an observation region is wider. The display unit 2 displays the composition image output from the control unit 5.

As a result of the irradiation of the radiation performed plural times, the radiographing system according to the exemplary embodiment of the present invention can perform the stitch imaging in which the spinal, the entire lower limb, or the entire body of the subject 10 is imaged.

It should be noted that the radiation detecting apparatus 7 may have a detecting function for automatically detecting the irradiation of the radiation from the radiation generating unit 8. The detecting function for automatically detecting the irradiation is a function for accumulating charges derived from the radiation in response to the detection of the radiation by the radiation detecting apparatus 7 when the radiation is emitted from the radiation generating unit 8.

Figure 2:
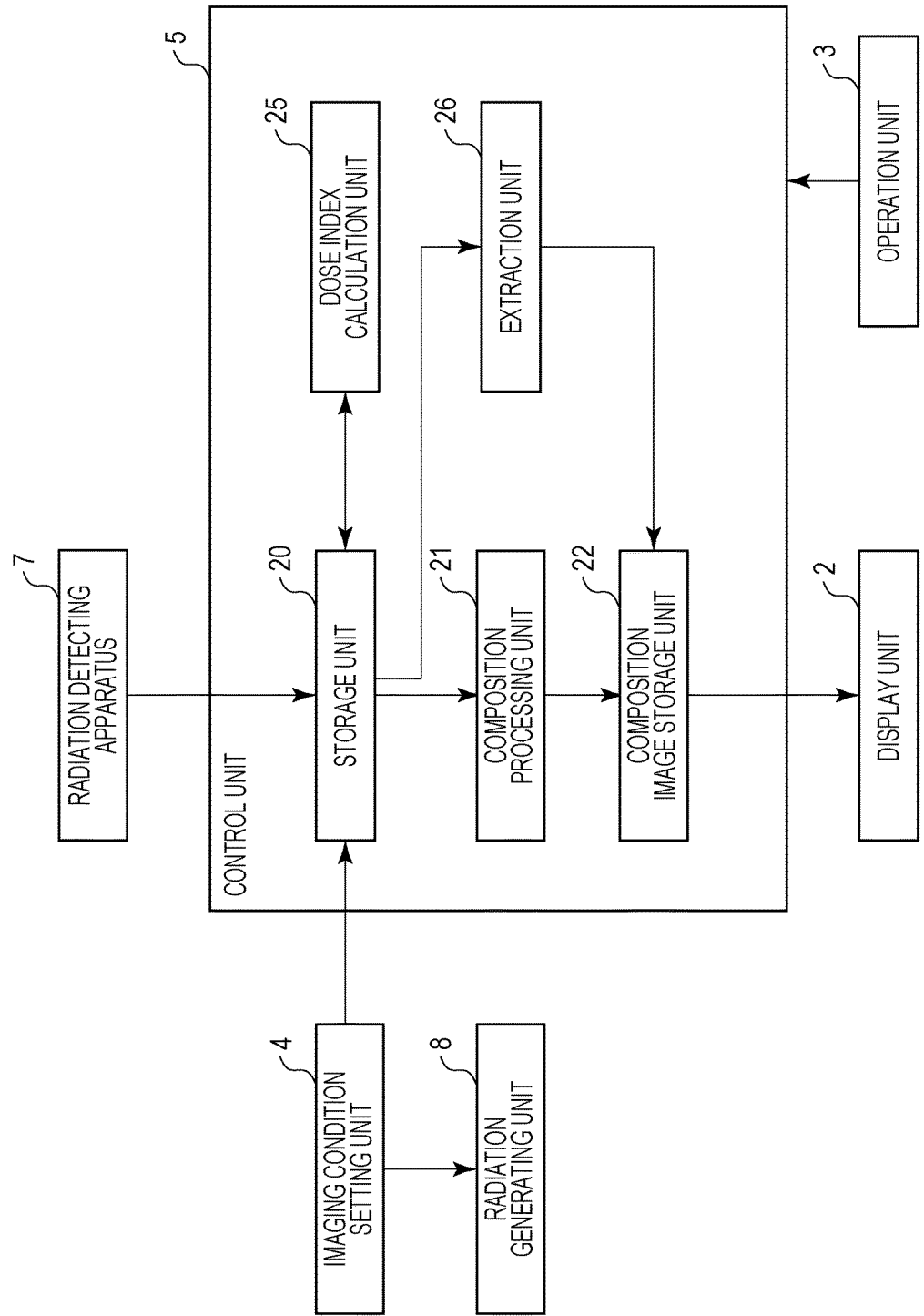
FIG. 2 illustrates a configuration of a control unit in the radiographing system according to the exemplary embodiment of the present invention.

As illustrated in FIG. 2, the control unit 5 includes a storage unit 20 configured to store the plurality of radiographic images output from the radiation detecting apparatus, a composition processing unit 21 configured to generate a composition image (lengthy image) by combining the plurality of radiographic images with one another, and a composition image storage unit 22 configured to store the composition image obtained by the composition by the composition processing unit 21. The control unit 5 also includes a dose index calculation unit 25 configured to respectively calculate dose indices from the plurality of radiographic images. The control unit 5 also includes an extraction unit (obtaining unit) 26 configured to obtain a representative dose index on the basis of the plurality of dose indices calculated by the dose index calculation unit 25. It should be noted that, according to the present exemplary embodiment, the descriptions have been made in a manner that the storage unit 20 are distinguished from the composition image storage unit 22, but these storage units may be a common storage unit (single storage unit) configured to store the plurality of radiographic images, the composition image, and other information.

The storage unit 20 stores the radiographic image output from the radiation detecting apparatus 7 together with the imaging condition set by the imaging condition setting unit 4. That is, in a case where the plurality of radiographic images are stored in the storage unit 20, the respective imaging conditions are attached to the plurality of radiographic images to be stored in the storage unit 20.

The storage unit 20 can store the radiographic image output from the radiation detecting apparatus 7 together with time information. Thus, the storage unit 20 can distinguish at which position the imaging is performed on the basis of the time information when the radiographic image is obtained and store the radiographic image.

The storage unit 20 can also store the plurality of radiographic images captured by the radiation detecting apparatus 7 while being associated with positional information (spatial arrangement information) of the radiation detecting apparatus 7. The storage unit 20 can output the plurality of radiographic images and the positional information to the composition processing unit 21.

The composition processing unit 21 combines the plurality of radiographic images stored in the storage unit 20 with one another to generate the composition image (lengthy image). Specifically, the composition processing unit 21 performs the composition on the basis of the respective pieces of positional information of the plurality of radiographic images output from the radiation detecting apparatus 7 to generate the composition image. Specifically, the composition processing unit 21 determines positional relationships (for example, an upper part, a central part, and a lower part) of the plurality of radiographic images output from the radiation detecting apparatus 7 on the basis of the positional information and performs the composition such that the respective radiographic images are overlapped with each other. In this manner, the composition processing unit 21 can generate the composition image (lengthy image) by combining the plurality of radiographic images with one another. In addition, the composition processing unit 21 can perform image processing such as gradation processing on the composition image.

The composition image storage unit 22 stores the composition image combined in the composition processing unit 21. That is, the composition image storage unit 22 stores the lengthy image obtained by combining the plurality of radiographic images with one another.

The dose index calculation unit 25 calculates the dose index from the radiographic image stored in the storage unit 20. It should be noted that the dose index calculation unit 25 may be connected to the radiation detecting apparatus 7, and the dose index may be calculated from the radiographic image output from the radiation detecting apparatus 7.

The dose index calculation unit 25 analyzes the radiographic image and calculates the dose index corresponding to the incident dose index to the radiation detecting apparatus 7 that detects the radiation. In a case where the plurality of radiographic images are captured by the radiation detecting apparatus 7, the dose index calculation unit 25 respectively calculates the dose indices from the plurality of radiographic images.

The dose index is, for example, Exposure Index (EI). The dose index is a value for evaluating a dose used in the radiographic imaging. The EI is an index standardized by International Electric Conference (IEC) as IEC62494-1.

Specifically, first, the dose index calculation unit 25 sets a target region in the radiographic image and calculates a representative pixel value in the target region. The representative pixel value is a pixel value such as an average value, a median value, and a mode value. The dose index calculation unit 25 converts the representative pixel value into a dose on the basis of a relationship between the already found incident dose and the pixel value. Then, the dose index calculation unit 25 multiplies the converted dose by a constant to calculate a dose index (EI). It should be noted that the dose index calculation unit 25 calculates the EI as the dose index, but a dose index other than the EI may be used as long as a determination on whether the dose reaching the radiation detecting apparatus 7 is relatively high or low can be performed on the basis of the dose index.

The dose index calculated by the dose index calculation unit 25 is stored in the storage unit 20 together with the radiographic image and the imaging condition. That is, the storage unit 20 stores the radiographic image output from the radiation detecting apparatus 7 together with the imaging condition of the radiation generating unit 8 set by the imaging condition setting unit 4 and the dose index calculated by the dose index calculation unit 25.

The extraction unit (obtaining unit) 26 obtains the representative dose index from among the plurality of dose indices calculated by the dose index calculation unit 25. The extraction unit (obtaining unit) 26 obtains the representative dose index in accordance with the number of the radiographic images constituting the composition image (lengthy image) generated by the composition processing unit 21. When the composition image is an image combined by using the two radiographic images, the extraction unit (obtaining unit) 26 obtains the representative dose index from among the two dose indices in the two radiographic images constituting the composition image. When the composition image is an image combined by using the three radiographic images, the extraction unit (obtaining unit) 26 obtains the representative dose index from among the three dose indices in the three radiographic images constituting the composition image.

Figures 3A, 3B:
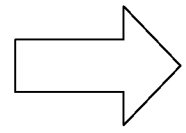
FIGS. 3A and 3B illustrate obtainment of a representative dose index in the radiographing system according to the exemplary embodiment of the present invention.

FIGS. 3A and 3B are explanatory diagrams for describing obtainment of the representative dose index by the extraction unit (obtaining unit) 26 according to the exemplary embodiment of the present invention. FIG. 3A illustrates the dose index and the imaging condition in the radiographic image stored in the storage unit 20. FIG. 3B illustrates a mode in which the extraction unit (obtaining unit) 26 obtains the representative dose index from among the plurality of dose indices.

Herein, a case will be considered where the three radiographic images are captured, and the composition image is generated. Image IDs are assigned to the respective radiographic images. Then, the dose indices (EI) are calculated for the respective radiographic images by the dose index calculation unit 25. In addition, the imaging condition of the radiation generating unit 8 (X-ray tube voltage, X-ray tube current, and irradiation time) are attached to the respective radiographic images.

As illustrated in FIG. 3A, with regard to an image ID 001 for the radiographic image captured as the first image, the dose index (EI) is 100, the X-ray tube voltage is V1, the X-ray tube current is I1, and the irradiation time is T1. With regard to an image ID 002 for the radiographic image captured as the second image, the dose index (EI) is 110, the X-ray tube voltage is V2, the X-ray tube current is 12, and the irradiation time is T2. With regard to an image ID 003 for the radiographic image captured as the third image, the dose index (EI) is 105, the X-ray tube voltage is V3, the X-ray tube current is 13, and the irradiation time is T3. In this manner, the storage unit 20 stores the radiographic image that has been subjected to the radiographic imaging, the dose index calculated by the dose index calculation unit 25, and the imaging condition of the radiation generating unit 8 while being associated with one another.

Representative Dose Index: Highest

Then, the extraction unit (obtaining unit) 26 obtains the representative dose index from among the plurality of dose indices calculated by the dose index calculation unit 25. As illustrated in FIG. 3B, the extraction unit (obtaining unit) 26 obtains the highest dose index from among the plurality of dose indices calculated by the dose index calculation unit 25 as the representative dose index. Specifically, the extraction unit (obtaining unit) 26 compares the dose indices (EI) attached to the plurality of radiographic images with one another. Herein, the extraction unit (obtaining unit) 26 compares the dose index (EI) of 100 in the image ID 001, the dose index (EI) of 110 in the image ID 002, and the dose index (EI) of 105 in the image ID 003 with one another. Then, the extraction unit (obtaining unit) 26 obtains the dose index (EI) of 110 in the image ID 002 which is the highest dose index as the representative dose index. The extraction unit (obtaining unit) 26 outputs dose index (EI) of 110, that is the highest dose index (EI), to the composition image storage unit 22 as the representative dose index. At this time, the image information of the image ID 002 having the dose index (EI) of 110 and the imaging condition (X-ray tube voltage, X-ray tube current, and irradiation time) are output to the composition image storage unit 22.

The composition image storage unit 22 stores the composition image combined in the composition processing unit 21 together with the representative dose index (dose index (EI): 110).

In addition, the composition image storage unit 22 can store the composition image together with the image information of the image ID 002 corresponding to the radiographic image that is the target where the representative dose index (dose index (EI): 110) is calculated. The display unit 2 displays the composition image together with the image information of the image ID 002 corresponding to the radiographic image that is the target where the representative dose index (dose index (EI): 110) is calculated. Thus, the operator can grasp the dose index corresponding to the radiographic image that is the target representative dose index in the composition image.

In addition, the composition image (lengthy image) captured by the radiographing apparatus 1 is transmitted to the PACS 13 (external apparatus) together with the representative dose index. In addition, the composition image may be transmitted to the PACS 13 together with the imaging condition associated with the representative dose index and the image ID 002 corresponding to the radiographic image that is the target where the representative dose index (dose index (EI): 110) is calculated.

The high definition monitor connected to the PACS 13 can display the composition image and the representative dose index. Thus, the operator can grasp the representative dose index in the composition image. In addition, the PACS 13 stores the representative dose index together with the composition image captured by the radiographing apparatus 1. Then, the PACS 13 can calculate a statistic value of the representative dose index such as an addition value or an average value of for each subject. In this manner, the operator can manage the dose of the imaged subject.

In addition, the composition image storage unit 22 can store the composition image together with the imaging condition with regard to the image ID 002 corresponding to the radiographic image that is the target where the representative dose index (dose index (EI): 110) is calculated. That is, the composition image storage unit 22 stores the imaging condition with regard to the image ID 002 (the X-ray tube voltage V2, the X-ray tube current 12, and the irradiation time T2) together with the composition image. The display unit 2 displays the composition image together with the imaging condition with regard to the image ID 002 corresponding to the radiographic image that is the target where the representative dose index (dose index (EI): 110) is calculated. Thus, the operator can grasp the dose index and imaging condition corresponding to the radiographic image that is the target representative dose index in the composition image.

Figure 4:
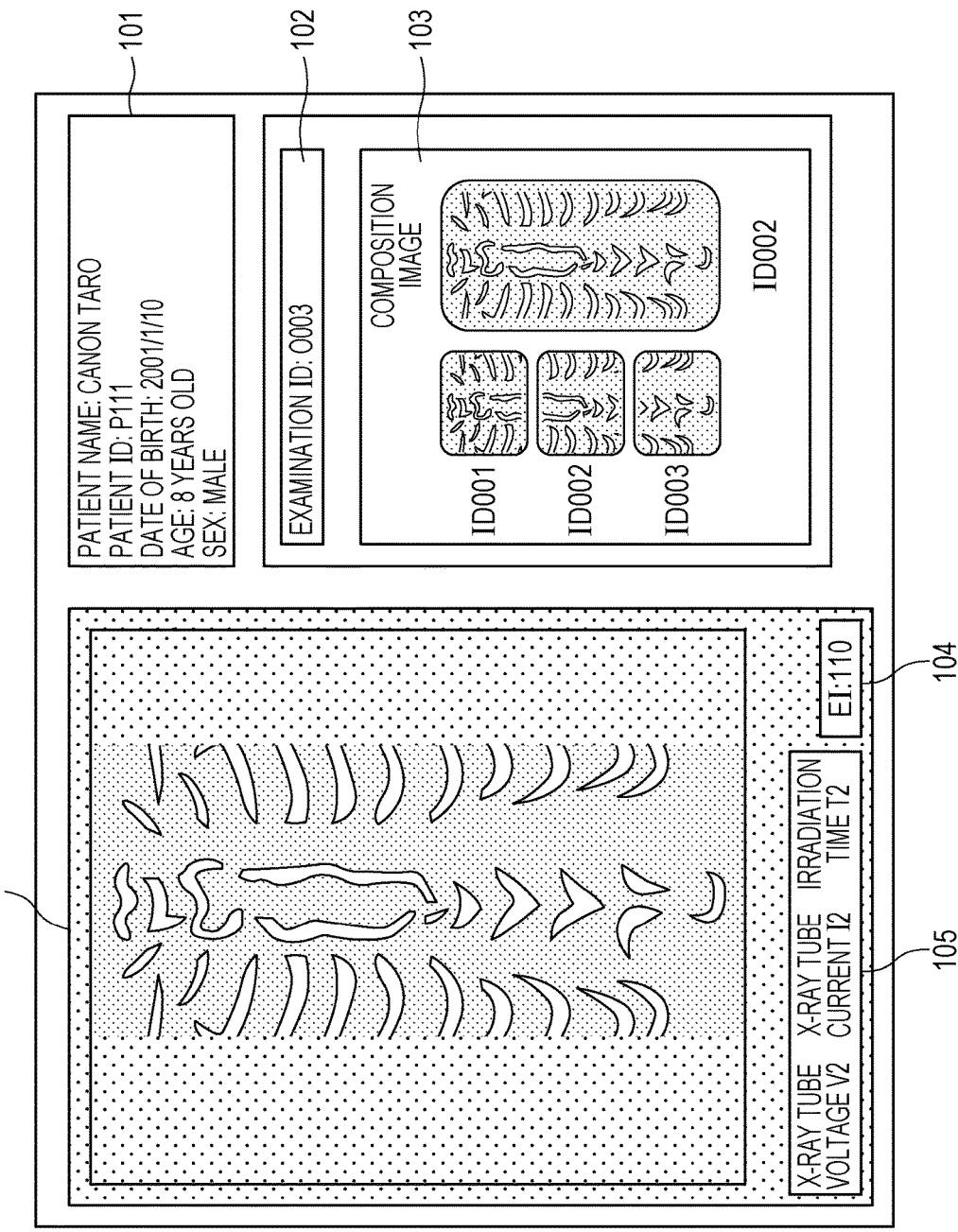
FIG. 4 illustrates a display mode of the radiographing system according to the exemplary embodiment of the present invention.

FIG. 4 illustrates a display mode of the display unit 2 in the radiographing system according to the exemplary embodiment of the present invention. The display unit 2 displays a composition image 100 obtained by the combination in the composition processing unit 21.

As illustrated in FIG. 4, the display unit 2 displays the composition image 100 obtained by the combination in the composition processing unit 21, subject information 101, examination information 102, a thumbnail image 103 of the composition image, a representative dose index 104 in the composition image, image information of the radiographic image that is the target where the representative dose index (dose index (EI): 110) is calculated, and an imaging condition 105 of the radiographic image. The display unit 2 displays at least the composition image 100 and the representative dose index 104 on the same screen.

The subject information 101 includes a name, an ID, a date of birth, a sex, and the like of the subject. The examination information 102 includes an examination ID.

The display unit 2 displays the representative dose index (dose index (EI): 110) 104 and the imaging condition (the X-ray tube voltage V2, the X-ray tube current 12, and the irradiation time T2) 105 at an end part of the composition image 100. The end part of the composition image 100 is a region on which the target region of the imaging site of the subject is not overlapped. Thus, the operator can grasp the value of the representative dose index in the composition image 100. In addition, the operator can grasp the imaging conditions in the composition image 100.

The display unit 2 displays the information of the image ID 002, corresponding to the radiographic image that is the target where the representative dose index (dose index (EI): 110) is calculated, surrounding the thumbnail image 103 of the composition image. Thus, the operator can grasp from which radiographic image the representative dose index in the composition image is obtained. It should be noted that the display unit 2 can also display the representative dose index 104 and the imaging condition 105 surrounding the thumbnail image 103 of the composition image.

Representative Dose Index: Average Value

The extraction unit (obtaining unit) 26 obtains the highest dose index from among the plurality of dose indices calculated by the dose index calculation unit 25 as the representative dose index according to the above-described exemplary embodiment, but an average value of the dose indices may be set as the representative dose index.

The extraction unit (obtaining unit) 26 obtains an average value from the dose index (EI) of 100 in the image ID 001, the dose index (EI) of 110 in the image ID 002, and the dose index (EI) of 105 in the image ID 003. At this time, 100+110+105/3–105 is obtained.

The extraction unit (obtaining unit) 26 outputs the average value of the dose indices (EI) of 105 to the composition image storage unit 22 as the representative dose index. At this time, the image information of the image ID 003 having the dose index (EI) of 105 that is the closest to the average value of the dose indices (EI) may also be output to the composition image storage unit 22. Then, the composition image storage unit 22 stores the composition image combined in the composition processing unit 21 together with the representative dose index (dose index (EI): 105).

Representative Dose Index: Median Value

The extraction unit (obtaining unit) 26 obtains a median value from the dose index (EI) of 100 in the image ID 001, the dose index (EI) of 110 in the image ID 002, and the dose index (EI) of 105 in the image ID 003. At this time, the dose index (EI) of 105 is obtained.

The extraction unit (obtaining unit) 26 outputs the median value of the dose indices (EI) of 105 to the composition image storage unit 22 as the representative dose index. Then, the composition image storage unit 22 stores the composition image combined in the composition processing unit 21 together with the representative dose index (dose index (EI): 105).

Representative Dose Index: Lowest

In addition, the extraction unit (obtaining unit) 26 may obtain the lowest dose index from among the plurality of dose indices calculated by the dose index calculation unit 25 as the representative dose index. Specifically, the dose indices (EI) attached to the plurality of radiographic images are compared with one another. As illustrated in FIG. 3A, the extraction unit (obtaining unit) 26 obtains the dose index (EI) of 100 in the image ID 001 corresponding to the lowest dose index as the representative dose index. The extraction unit (obtaining unit) 26 outputs the lowest dose index (EI) of 100 to the composition image storage unit 22 as the representative dose index.

Imaging Condition: Highest mAs Value

In addition, the extraction unit (obtaining unit) 26 may obtain the representative dose index on the basis of the imaging conditions for the plurality of radiographic images.

As illustrated in FIG. 3A, with regard to the image ID 001 for the radiographic image captured as the first image, the dose index (EI) is 100, the X-ray tube voltage is V1, the X-ray tube current is I1, and the irradiation time is T1. With regard to the image ID 002 for the radiographic image captured as the second image, the dose index (EI) is 110, the X-ray tube voltage is V2, the X-ray tube current is I2, and the irradiation time is T2. With regard to the image ID 003 for the radiographic image captured as the third image, the dose index (EI) is 105, the X-ray tube voltage is V3, the X-ray tube current is I3, and the irradiation time is T3.

The extraction unit (obtaining unit) 26 obtains the X-ray tube current and the irradiation time corresponding to the imaging condition under which a value (mAs value) obtained by multiplying the X-ray tube current by the irradiation time becomes the highest. Herein, a case will be considered where the mAs value under the imaging condition where the X-ray tube current is I3 and the irradiation time is T3 is the highest. The extraction unit (obtaining unit) 26 obtains the dose index (EI) when the X-ray tube current is I3 and the irradiation time is T3.

Then, the display unit 2 displays the composition image together with the image information of the image ID 003 corresponding to the radiographic image of the target where the representative dose index (dose index (EI)) is calculated. Thus, the operator can grasp that the representative dose index in the composition image is the dose index based on the imaging condition under which the mAs value is the highest.

Other Than the Representative Dose Index (EI)

It should be noted that, according to the above-described exemplary embodiment, the descriptions have been given while the EI is used as the dose index, but other dose indices may be also used as long as the dose index is identified. For example, a target value serving as a reference when the radiographic image is optimally irradiated (target exposure index) may be set, and the dose index (Deviation Index: DI) may be obtained from the EI calculated by the dose index calculation unit 25.

In addition, the extraction unit (obtaining unit) 26 may obtain the representative dose index on the basis of the positional information attached to the plurality of radiographic images. Herein, the composition processing unit 21 determines the positional relationships (for example, the upper part, the central part, and the lower part) of the plurality of radiographic images output from the radiation detecting apparatus 7 on the basis of the positional information and combines the respective radiographic images to as to overlap with one another. For example, the extraction unit (obtaining unit) 26 may obtain the dose index attached to the captured radiographic image at a position corresponding to the central part as the representative dose index. The extraction unit (obtaining unit) 26 may also obtain the dose index attached to the captured radiographic image at a position corresponding to the upper part as the representative dose index. The change in this obtaining position (upper part, central part, and lower part) can be performed by the operation unit.

Figure 5:
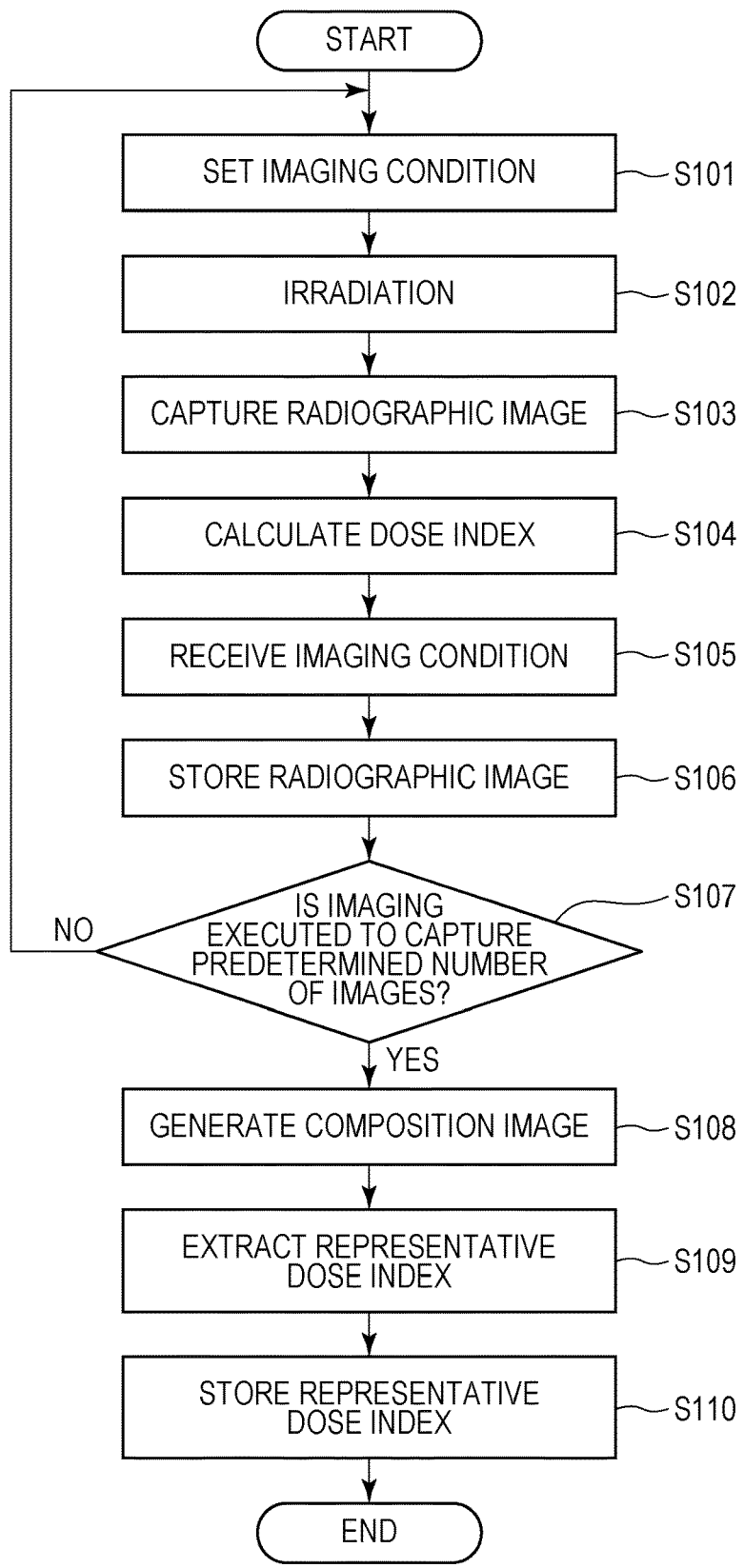
FIG. 5 is a flow chart illustrating an operation of the radiographing system according to the exemplary embodiment of the present invention.

Here, the operation of the radiographing system according to the exemplary embodiment of the present invention will be described with reference to a flow chart illustrated in FIG. 5.

First, the operator uses the imaging condition setting unit 4 to set the imaging condition (X-ray tube voltage, X-ray tube current, and irradiation time) with respect to the radiation generating unit 8. (S101)

The operator accommodates the radiation detecting apparatus 7 in the imaging table 6, and the subject 10 is installed along the longitudinal direction of the imaging table 6. In this state, while the radiation detecting apparatus 7 is slid along the longitudinal direction of the imaging table 6, radiation is emitted from the radiation generating unit 8 plural times. (S102)

The radiation emitted plural times while the radiation detecting apparatus 7 is slid along the vertical direction transmits through the subject 10 and reaches the radiation detecting apparatus 7 to be detected. The radiation detecting apparatus 7 detects the radiation emitted from the radiation generating unit 8 plural times. The radiation detecting apparatus 7 images the radiation emitted from the radiation generating unit 8 plural times. Then, the radiation detecting apparatus 7 outputs the plurality of captured radiographic images. (S103)

The dose index calculation unit 25 respectively calculates the dose indices from the plurality of radiographic images captured by the radiation detecting apparatus 7. The dose index calculation unit 25 outputs the respective dose indices. The storage unit 20 stores the dose indices calculated by the dose index calculation unit 25. An initial setting for the dose indices calculated by the dose index calculation unit 25 is the EI. The dose index calculation unit 25 can select so as to calculate the dose indices other than the EI (such as the DI). (S104). The imaging condition setting unit 4 sets the imaging condition for the radiation in the radiation generating unit 8 and controls the radiation generating unit 8. The storage unit 20 stores the imaging condition set by the imaging condition setting unit 4 together with the radiographic image. (S105)

The storage unit 20 stores the plurality of radiographic images captured in S103. At this time, the storage is performed so as to distinguish the radiographic images from one another depending on at which position the radiographic image is captured. Specifically, in a case where three radiographic images are captured, the storage unit 20 stores the first radiographic image, the dose index calculated from the first radiographic image by the dose index calculation unit 25, and the imaging condition of the radiation generating unit 8 when the first radiographic image is captured while being associated with one another. The storage unit 20 stores the second radiographic image, the dose index calculated from the second radiographic image by the dose index calculation unit 25, and the imaging condition of the radiation generating unit 8 when the second radiographic image is captured while being associated with one another. Similarly, the storage unit 20 stores the third radiographic image, the dose index calculated from the third radiographic image by the dose index calculation unit 25, and the imaging condition of the radiation generating unit 8 when the third radiographic image is captured while being associated with one another. (S106)

The control unit 5 checks whether or not the imaging is executed to capture the desired number of images. For example, in a case where three radiographic images are captured to generate the composition image (lengthy image), when the three radiographic images are captured in S103, the flow proceeds to step S108. When the three radiographic images are not captured in S103, the flow proceeds to step S101. (S107)

The composition processing unit 21 combines the plurality of radiographic images captured in S103 with one another on the basis of the positional information to generate the composition image (lengthy image). Then, the composition image storage unit 22 stores the composition image combined in the composition processing unit 21. (S108)

The extraction unit (obtaining unit) 26 obtains the representative dose index from among the plurality of dose indices calculated in S104. The extraction unit (obtaining unit) 26 obtains the representative dose index from among the plurality of dose indices in the plurality of radiographic images constituting the composition image (lengthy image) generated in the composition processing unit 21. It should be noted that a characteristic (such as the highest, the lowest, the average value, or the median value) of the representative dose index obtained by the extraction unit (obtaining unit) 26 can be selected by the operator via the operation unit 3. That is, the radiographing system according to the exemplary embodiment of the present invention is provided with a selection unit configured to select the characteristic (obtaining reference) of the representative dose index obtained on the basis of the plurality of dose indices. For example, the operator can select via the operation unit 3 whether the highest dose index among the plurality of dose indices is obtained, the lowest dose index is obtained, the average value of the plurality of dose indices is obtained, or the median value of the plurality of dose indices is obtained as the representative dose index. This is because there is a possibility that a target for managing the representative dose index may differ depending on hospitals. (S109)

The composition image storage unit 22 stores the composition image (lengthy image) combined in the composition processing unit 21 together with the representative dose index. That is, the representative dose index is attached to the composition image and stored in the composition image storage unit 22. (S110)

As described above, the radiographing system according to the present exemplary embodiment is provided with the dose index calculation unit 25 configured to respectively analyze the plurality of radiographic images and calculate the plurality of dose indices corresponding to the plurality of radiographic images, the extraction unit (obtaining unit) 26 configured to obtain the representative dose index from among the plurality of dose indices calculated by the dose index calculation unit 25, and the composition image storage unit 22 configured to store the composition image together with the representative dose index. That is, the radiographing system is provided with a dose index calculation unit (the dose index calculation unit 25) respectively calculate the dose indices from the plurality of radiographic images, an obtaining unit (the extraction unit (obtaining unit) 26) configured to obtain the representative dose index from among the plurality of dose indices calculated by the dose index calculation unit, and a storage unit (the composition image storage unit 22) configured to store the representative dose index together with the composition image. Thus, it is possible to perform the dose management in the composition image by attaching the representative dose index to the composition image.

Second Exemplary Embodiment

Figure 6:
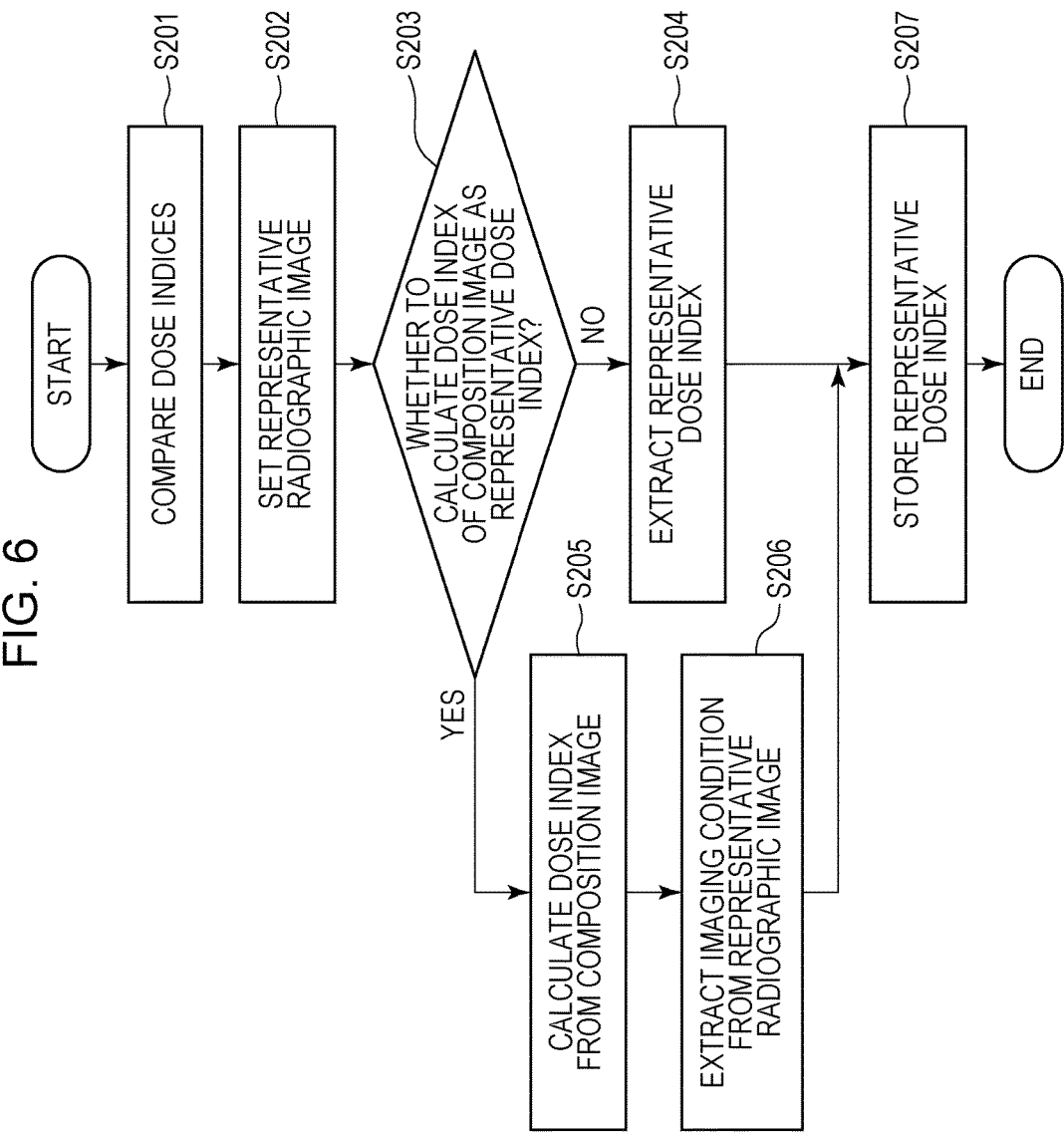
FIG. 6 is a flow chart illustrating the operation of the radiographing system according to another exemplary embodiment of the present invention.

The radiographing system according to a second exemplary embodiment of the present invention will be described with reference to FIG. 6. A difference from the first exemplary embodiment resides in that the dose index calculation unit 25 calculates the dose index from the composition image (lengthy image) and sets the calculated dose index as the representative dose index.

Since the configuration according to the present exemplary embodiment is similar to the first exemplary embodiment, descriptions thereof will be omitted. Here, an operation of the radiographing system according to the exemplary embodiment of the present invention will be described with reference to a flow chart illustrated in FIG. 6.

The extraction unit (obtaining unit) 26 obtains the highest dose index and the lowest dose index as the representative dose indices from among the plurality of dose indices calculated by the dose index calculation unit 25. Specifically, the dose indices (EI) attached to the plurality of radiographic images are compared with one another. At this time, the extraction unit (obtaining unit) 26 compares the dose index (EI) of 100 in the image ID 001, the dose index (EI) of 110 in the image ID 002, and the dose index (EI) of 105 in the image ID 003 with one another. (S201)

Then, in a case where the representative dose index is managed by using the highest dose index, the control unit 5 identifies the radiographic image corresponding to the highest dose index. As illustrated in FIGS. 3A and 3B, the control unit 5 sets the radiographic image having the image ID 002 corresponding to the highest dose index as the representative radiographic image. It should be noted that, in a case where the representative dose index is managed by using the lowest dose index, the control unit 5 identifies the radiographic image corresponding to the lowest dose index. (S202)

The operator performs a setting via the operation unit 3 as to whether or not the dose index of the composition image is calculated as the representative dose index. In a case where the dose index of the composition image is calculated as the representative dose index, the flow proceeds to S205. In a case where the dose index of the composition image is not calculated as the representative dose index, the flow proceeds to S204. (S203)

In a case where the dose index of the composition image is not calculated as the representative dose index, the extraction unit (obtaining unit) 26 obtains the representative dose index from among the plurality of dose indices calculated in S201. The extraction unit (obtaining unit) 26 obtains the representative dose index from among the plurality of dose indices in the plurality of radiographic images constituting the composition image generated by the composition processing unit 21. The obtained representative dose index is output to the composition image storage unit 22. (S204)

In a case where the dose index of the composition image is calculated as the representative dose index, the dose index calculation unit 25 calculates the dose index corresponding to the incident dose index to the radiation detecting apparatus 7 from the composition image. It should be noted that the composition processing unit 21 and the dose index calculation unit 25 in FIG. 2 are connected to each other at this time. The dose index is, for example, the EI. The dose index calculation unit 25 sets a target region in the composition image and calculates a representative pixel value in the target region. The representative pixel value is a pixel value such as an average value, a median value, and a mode value. Then, the dose index calculation unit 25 converts the representative pixel value into a dose on the basis of the relationship between the already found incident dose and the pixel value. The dose index calculation unit 25 multiplies the converted dose by a constant to calculate a dose index (EI) from the composition image. The dose index of the composition image (EI) corresponding to the representative dose index is output to the composition image storage unit 22. (S205)

The control unit 5 obtains the imaging condition in the radiographic image corresponding to the target of the representative radiographic image set in S202. In a case where the radiographic image having the image ID 002 is set as the representative radiographic image, the control unit 5 obtains the imaging condition (X-ray tube voltage, X-ray tube current, and irradiation time) corresponding to the radiographic image of the image ID 002. Then, the imaging condition (X-ray tube voltage, X-ray tube current, and irradiation time) corresponding to the radiographic image of the image ID 002 is output to the composition image storage unit 22. (S206)

The composition image storage unit 22 stores the composition image (lengthy image) combined in the composition processing unit 21 together with the representative dose index. That is, the representative dose index calculated in S205 is attached to the composition image and stored in the composition image storage unit 22. In addition, the composition image storage unit 22 can store the imaging condition (X-ray tube voltage, X-ray tube current, and irradiation time) obtained in S206 while being attached to the composition image. (S207)

As described above, according to the present exemplary embodiment, since the dose index is calculated from the composition image (lengthy image), and the calculated dose index is set as the representative dose index, it is possible to perform the dose management of the composition image with regard to the dose index of the composition image itself.

Third Exemplary Embodiment

Figure 7:
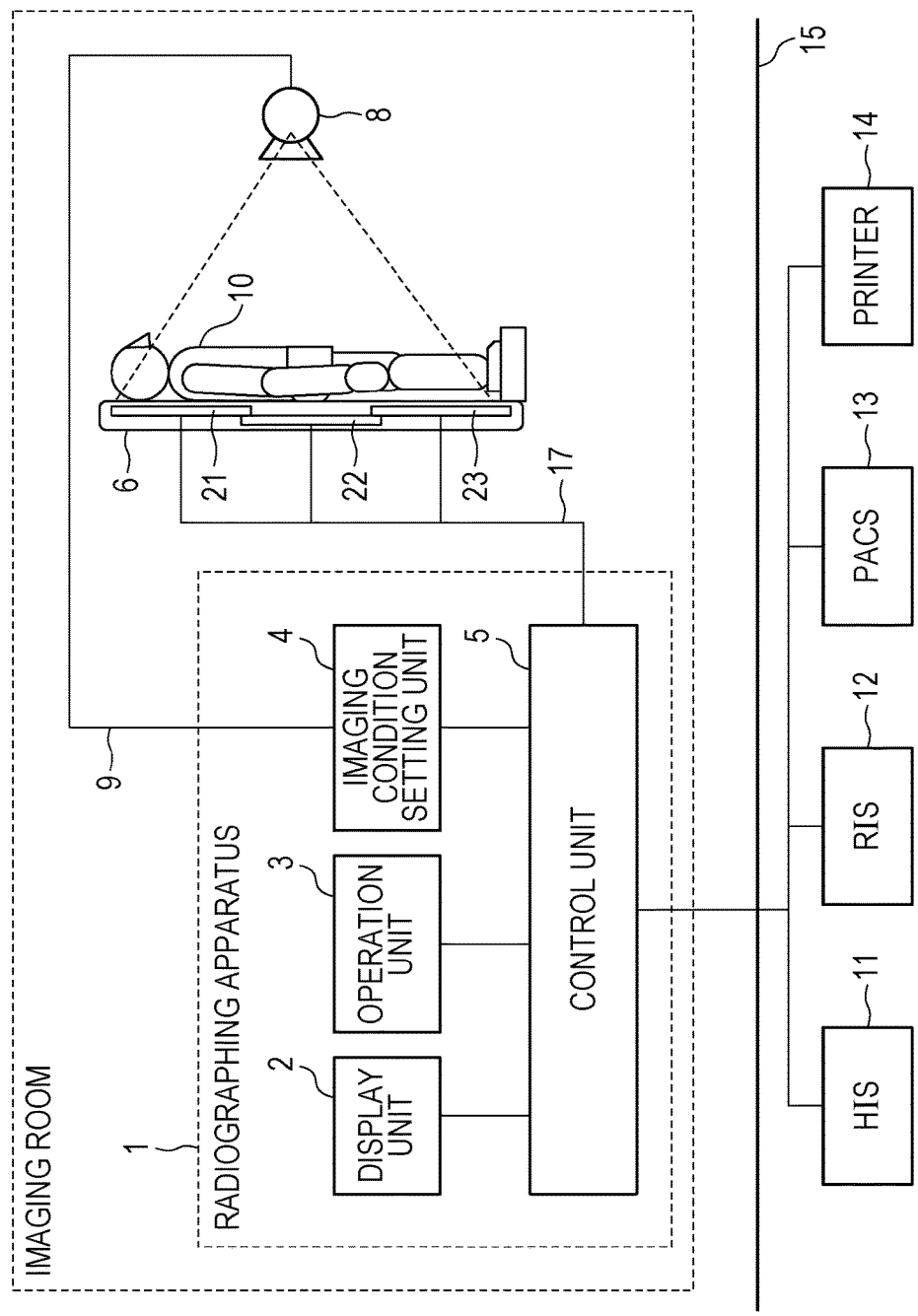
FIG. 7 illustrates an overall configuration of the radiographing system according to still another exemplary embodiment of the present invention.

The radiographing system according to a third exemplary embodiment of the present invention will be described with reference to FIG. 7 and FIG. 8. A difference from the first and second exemplary embodiments resides in that radiographic images are captured by a plurality of radiation detecting apparatuses 31, 32, and 33, and dose indices are calculated from the respective radiographic images.

The plurality of radiation detecting apparatuses 31, 32, and 33 are accommodated in the imaging table 6. The imaging table 6 is a rectangular casing, and the inside of the casing is hollow. In addition, the imaging table 6 has a function for holding the plurality of radiation detecting apparatuses 31, 32, and 33.

The radiation detecting apparatus 31, the radiation detecting apparatus 32, and the radiation detecting apparatus 33 are respectively arranged on the imaging table 6 in the longitudinal direction of the imaging table 6. At this time, the plurality of radiation detecting apparatuses are arranged while partially overlapped with the radiation detecting apparatus. For example, as illustrated in FIG. 7, the radiation detecting apparatus 31 and the radiation detecting apparatus 32 are arranged such that parts of the radiation detecting apparatuses are spatially overlapped with each other. At this time, imaging executable regions of the radiation detecting apparatus 31 and the radiation detecting apparatus 32 are overlapped with each other. Similarly, the radiation detecting apparatus 32 and the radiation detecting apparatus 33 are arranged such that parts of the radiation detecting apparatuses are spatially overlapped with each other. At this time, imaging executable regions of the radiation detecting apparatus 32 and the radiation detecting apparatus 33 are overlapped with each other. In addition, the radiation detecting apparatus 32 is arranged on a rear side of the radiation detecting apparatus 31 and the radiation detecting apparatus 33, that is, arranged at a position far from the radiation generating unit 8. An angle is set at which the radiation is incident so as to be perpendicular to the center of the radiation detecting apparatus 32. The radiation emitted from the radiation generating unit 8 towards the plurality of radiation detecting apparatuses 31, 32, and 33 transmits through the subject 10 and reaches the plurality of radiation detecting apparatuses 31, 32, and 33 to be detected at the same time. The radiographing apparatus 1 is connected to the plurality of radiation detecting apparatuses 31, 32, and 33 via the cable 17. It should be noted that, since the other configurations of FIG. 7 is similar to FIG. 1, descriptions thereof will be omitted.

Figure 8:
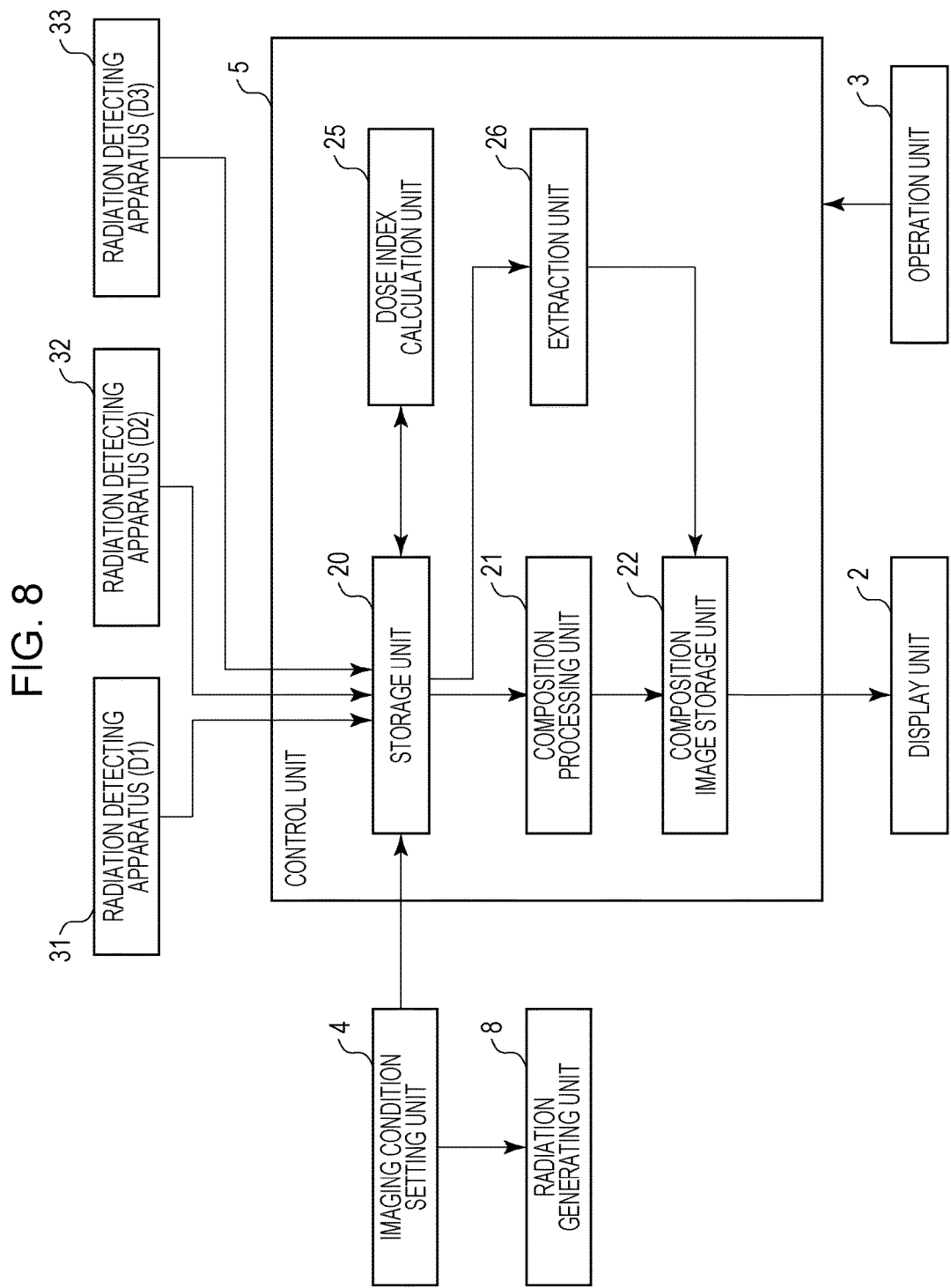
FIG. 8 illustrates an internal configuration of the radiographing system according to the exemplary embodiment of the present invention.

As illustrated in FIG. 8, the storage unit 20 stores the image data (radiographic images) output from the plurality of radiation detecting apparatuses 31, 32, and 33. As illustrated in FIG. 8, the radiation detecting apparatus 31, 32, and 33 are respectively illustrated as a radiation detecting apparatus (D1), a radiation detecting apparatus (D2), and a radiation detecting apparatus (D3).

The storage unit 20 can store the image data output from the radiation detecting apparatus 31, 32, and 33 together with the time information. Thus, the storage unit 20 can store the radiographic images output from the radiation detecting apparatus 31, 32, and 33 while distinguishing whether or not the radiographic images are obtained at the same time on the basis of the time information when the radiographic image is obtained.

The dose index calculation unit 25 calculates the dose indices from the plurality of radiographic images captured by the plurality of radiation detecting apparatuses 31, 32, and 33. The dose index calculation unit 25 outputs the dose indices. The storage unit 20 stores the dose indices calculated by the dose index calculation unit 25 while being associated with the plurality of radiographic images. Then, the extraction unit (obtaining unit) 26 obtains the representative dose index from among the plurality of dose indices in the plurality of radiographic images captured by the plurality of radiation detecting apparatuses 31, 32, and 33. The composition image storage unit 22 stores the composition image (lengthy image) combined in the composition processing unit 21 together with the representative dose index. That is, the representative dose index is attached to the composition image to be stored in the composition image storage unit 22. Thus, it is possible to perform the dose management in the composition image by attaching the representative dose index to the composition image based on the plurality of radiographic images captured by the plurality of radiation detecting apparatuses 31, 32, and 33.

It should be noted that, since the other configurations of FIG. 8 is similar to FIG. 2, descriptions thereof will be omitted.

Thus, the exemplary embodiments of the present invention can also be realized by processing in which a program for realizing one or more functions according to the above-described exemplary embodiments (in particular, the dose index management method) is supplied to a system or an apparatus via a network or a storage medium, and one or more processors in a computer of the system or the apparatus reads out and executes the program. In addition, the exemplary embodiments of the present invention can also be realized by a circuit that realizes one or more functions (for example, an application specific integrated circuit (ASIC)).

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-135413 filed Jul. 7, 2016, which is hereby incorporated by reference herein in its entirety.

What is claimed is:

1. A radiographing system that generates a composition image by combining a plurality of radiographic images with one another, the radiographing system comprising:
at least one memory; and
at least one processor that is configured to cause the radiographing system to perform operations comprising:
analyzing each of the plurality of radiographic images and calculate a plurality of dose indices corresponding to the plurality of radiographic images;
obtaining a representative dose index from among the plurality of calculated dose indices; and
storing the representative dose index together with the composition image.

2. The radiographing system according to claim 1, wherein the operations further comprising, analyzing each of the radiographic images and for each radiographic image calculating a dose index corresponding to an incident dose index received at a radiation detecting apparatus that detects radiation.

3. The radiographing system according to claim 1, wherein the operations further comprising, storing the radiographic image together with an imaging condition of a radiation, and the dose index.

4. The radiographing system according to claim 1, wherein the operations further comprising, obtaining the representative dose index in accordance with the number of the plurality of radiographic images constituting the composition image.

5. The radiographing system according to claim 1, wherein the operations further comprising, comparing the dose indices corresponding to the plurality of radiographic images with one another and obtaining a highest dose index as the representative dose index.

6. The radiographing system according to claim 1, wherein the operations further comprising, comparing the dose indices corresponding to the plurality of radiographic images with one another and obtaining a lowest dose index as the representative dose index.

7. The radiographing system according to claim 1, the operations further comprising, obtaining an average value of the dose indices corresponding to the plurality of radiographic images as the representative dose index.

8. The radiographing system according to claim 1, wherein the operations further comprising, comparing the dose indices corresponding to the plurality of radiographic images with one another and obtaining the dose index having a median value as the representative dose index.

9. The radiographing system according to claim 1, wherein the operations further comprising, obtaining the dose index corresponding to the captured radiographic image at a position corresponding to a central part as the representative dose index on a basis of positional information attached to the plurality of radiographic images.

10. The radiographing system according to claim 1, wherein the operations further comprising:
storing the composition image together with image information of one of the plurality of radiographic images that corresponds to a target where the representative dose index is calculated.

11. The radiographing system according to claim 1, further comprising:
a display, to display the composition image and the representative dose index on a same screen.

12. The radiographing system according to claim 11, wherein the operations further comprising:
displaying the composition image together with an imaging condition of one of the plurality of radiographic images that corresponds to a target where the representative dose index is calculated.

13. The radiographing system according to claim 1, wherein the operations further comprising:
selecting a characteristic of the representative dose index obtained on a basis of the plurality of dose indices.

14. The radiographing system according to claim 1, wherein the operations further comprising:
calculating each of the dose indices from the composition image and setting the calculated dose index as the representative dose index.

15. The radiographing system according to claim 1, wherein the operations further comprising:
calculating the plurality of dose indices from the plurality of radiographic images captured by a plurality of radiation detecting apparatus, and obtaining the representative dose index from among the plurality of dose indices.

16. A dose index management method comprising:
analyzing, by at least one processor, each of a plurality of radiographic images and calculating a plurality of dose indices corresponding to the plurality of radiographic images;

obtaining, by at least one processor, a representative dose index from the plurality of calculated dose indices; and storing, by at least one processor, a composition image obtained by combining the plurality of radiographic images with one another together with the representative dose index.

17. A non-transitory computer-readable storage medium that stores a program that when run on a computer causes the computer to execute the steps of the dose index management method according to claim 16.

* * * * *